United States Patent
Zha et al.

(10) Patent No.: US 11,459,571 B2
(45) Date of Patent: Oct. 4, 2022

(54) PROTEIN EXTRACTION METHOD WITHOUT LYSING CELLS

(71) Applicants: Jian Zha, Xi'an (CN); Zhiqiang Liu, Xi'an (CN); Guoli Gong, Xi'an (CN); Runcong Sun, Xi'an (CN)

(72) Inventors: Jian Zha, Xi'an (CN); Zhiqiang Liu, Xi'an (CN); Guoli Gong, Xi'an (CN); Runcong Sun, Xi'an (CN)

(73) Assignee: SHAANXI UNIVERSITY OF SCIENCE AND TECHNOLOGY, Xi'an (CN)

( * ) Notice: Subject to any disclaimer, the term of this patent is extended or adjusted under 35 U.S.C. 154(b) by 70 days.

(21) Appl. No.: 17/229,546

(22) Filed: Apr. 13, 2021

(65) Prior Publication Data

US 2022/0112507 A1 Apr. 14, 2022

(30) Foreign Application Priority Data

Oct. 13, 2020 (CN) .......................... 202011094821.8

(51) Int. Cl.
 *C12N 9/96* (2006.01)
 *C12N 15/70* (2006.01)
 *C12N 15/62* (2006.01)

(52) U.S. Cl.
 CPC ............. *C12N 15/62* (2013.01); *C12N 15/70* (2013.01); *C07K 2319/61* (2013.01)

(58) Field of Classification Search
 CPC ........... C12N 9/96; C12N 15/70; C12N 15/62
 See application file for complete search history.

(56) References Cited

PUBLICATIONS

Komioka et al., Anal. Biochem., 439, 212-127, Aug. 2013.*

* cited by examiner

*Primary Examiner* — Maryam Monshipouri

(74) *Attorney, Agent, or Firm* — SZDC Law P.C.

(57) ABSTRACT

A method for extracting protein without lysing cells includes: step 1: combining a penetrating peptide CPP gene having a sequence as set forth in SEQ ID NO: 1 and a bacterial lyase T4L gene having a sequence as set forth in SEQ ID NO: 2 through a flexible connecting peptide GGGGS gene having a sequence as set forth in SEQ ID NO: 3 to form a fusion enzyme CPP-T4L gene having a sequence as set forth in SEQ ID NO: 4; step 2: inserting the fusion enzyme CPP-T4L gene, and obtaining a recombinant host strain; step 3: cloning a target protein expression gene, and then constructing a recombinant expression strain; step 4: first inducing the expression of the target protein expression gene; starting the expression of the fusion enzyme CPP-T4L gene, and releasing a target protein; step 5: collecting cell lysis supernatant to recover the target protein.

7 Claims, 3 Drawing Sheets

Specification includes a Sequence Listing.

SEQUENCE LISTING

```
<160> NUMBER OF SEQ ID NOS: 4

<210> SEQ ID NO 1
<211> LENGTH: 54
<212> TYPE: DNA
<213> ORGANISM: Unkown
<220> FEATURE:
<223> OTHER INFORMATION: Penetrating peptide CPP

<400> SEQUENCE: 1
aaacttgccc tgaaattagc acttaaagcg ttgaaggctg cattgaaatt agcc          54

<210> SEQ ID NO 2
<211> LENGTH: 492
<212> TYPE: DNA
<213> ORGANISM: Unknown
<220> FEATURE:
<223> OTHER INFORMATION: Baterial lyase T4L
<220> FEATURE:
<223> OTHER INFORMATION: T4L

<400> SEQUENCE: 2
atgaatatat ttgaaatgtt acgtatagat gaaggtctta gacttaaaat ctataaagac    60
acagaaggct attacactat tggcatcggt catttgctta caaaaagtcc atcacttaat   120
gctgctaaat ctgaattaga taaagctatt gggcgtaatt gcaatggtgt aattacaaaa   180
gatgaggctg aaaaactctt taatcaggat gttgatgctg ctgttcgcgg aattctgaga   240
aatgctaaat taaaaccggt ttatgattct cttgatgcgg ttcgtcgctg tgcattgatt   300
aatatggttt tccaaatggg agaaaccggt gtggcaggat ttactaactc tttacgtatg   360
cttcaacaaa aacgctggga tgaagcagca gttaacttag ctaaaagtag atggtataat   420
caaacaccta atcgcgcaaa acgagtcatt acaacgttta gaactggcac ttgggacgcg   480
tataaaaatc ta                                                       492

<210> SEQ ID NO 3
<211> LENGTH: 15
<212> TYPE: DNA
<213> ORGANISM: Unknown
<220> FEATURE:
<223> OTHER INFORMATION: Flexible connecting peptide GGGGS
<220> FEATURE:
<223> OTHER INFORMATION: GGGGS

<400> SEQUENCE: 3
ggtggtggtg gcagc                                                     15

<210> SEQ ID NO 4
```

```
<211> LENGTH: 561
<212> TYPE: DNA
<213> ORGANISM: Unknown
<220> FEATURE:
<223> OTHER INFORMATION: Fusion enzyme CPP-T4L
<220> FEATURE:
<223> OTHER INFORMATION: Unkown

<400> SEQUENCE: 4
aaacttgccc tgaaattagc acttaaagcg ttgaaggctg cattgaaatt agccggtggt      60
ggtggcagca tgaatatatt tgaaatgtta cgtatagatg aaggtcttag acttaaaatc     120
tataaagaca cagaaggcta ttacactatt ggcatcggtc atttgcttac aaaaagtcca     180
tcacttaatg ctgctaaatc tgaattagat aaagctattg ggcgtaattg caatggtgta     240
attacaaaag atgaggctga aaaactcttt aatcaggatg ttgatgctgc tgttcgcgga     300
attctgagaa atgctaaatt aaaaccggtt tatgattctc ttgatgcggt tcgtcgctgt     360
gcattgatta atatggtttt ccaaatggga gaaaccggtg tggcaggatt tactaactct     420
ttacgtatgc ttcaacaaaa acgctgggat gaagcagcag ttaacttagc taaaagtaga     480
tggtataatc aaacacctaa tcgcgcaaaa cgagtcatta caacgtttag aactggcact     540
tgggacgcgt ataaaaatct a                                               561
```

PROTEIN EXTRACTION METHOD WITHOUT LYSING CELLS

The present application claims priority to Chinese Patent Application No. 202011094821.8, filed on Oct. 13, 2020, which is incorporated by reference for all purposes as if fully set forth herein.

FIELD OF THE INVENTION

The invention relates to the field of genetic engineering, and particularly, relates to a protein extraction method without cell lysis.

BACKGROUND OF THE INVENTION

Traditional protein extraction methods mainly include mechanical disintegration, ultrasonic disintegration, repeated freezing and thawing, and surfactant treatment and enzymatic hydrolysis. These methods involve cell lysis in the operation process, which is complicated and difficult to operate and requires special equipment. Especially in the industrial production process, the cell crushing operation process is complicated, the operation time is long, and the equipment occupancy rate is high, which greatly reduces the production efficiency and increases the production cost.

In addition to the above methods, secretory expression is also a protein production method that has been studied and applied. There are, however, also problems in the construction of expression vectors, limited secretion efficiency, the removal of signal peptides, and limited protein yield. Therefore, there is a need for a widely applicable and more efficient protein extraction method to reduce production costs and improve economic benefits.

SUMMARY OF THE INVENTION

In one embodiment, the present application provides a method for extracting protein without lysing cells. The method includes: step 1: combining a penetrating peptide CPP gene having a sequence as set forth in SEQ ID NO: 1 and a bacterial lyase T4L gene having a sequence as set forth in SEQ ID NO: 2 through a flexible linker peptide GGGGS gene having a sequence as set forth in SEQ ID NO: 3 to form a fusion enzyme CPP-T4L gene having a sequence as set forth in SEQ ID NO: 4; step 2: inserting the fusion enzyme CPP-T4L gene into a fusion enzyme expression vector through cloning, and then transferring the fusion enzyme expression vector into an expression strain to obtain a recombinant host strain; step 3: inserting a target protein expression gene into a target protein expression vector, and then transferring the target protein expression vector into a recombinant host strain to construct a recombinant expression strain; step 4: in an expression system of the recombinant expression strain, first inducing the expression of the target protein expression gene; after the expression of the target protein expression gene is completed, adding an IPTG (isopropyl β-D-1-thiogalactopyranoside) solution to the expression system to start the expression of the fusion enzyme CPP-T4L gene and release a target protein; and step 5: after filtering to remove cell residues, collecting a cell lysis supernatant to obtain the target protein.

In another embodiment, in step 2, the fusion enzyme expression vector is *Escherichia coli* expression vector pGS21a, and the expression strain is *Escherichia coli* BL21* (DE3).

In another embodiment, in step 2, the fusion enzyme expression vector is transferred into the expression strain by a calcium chloride method.

In another embodiment, in step 3, the target protein expression vector is a pBAD/His vector.

In another embodiment, the target protein is lysostaphin, and arabinose is added in step 4 to induce the expression of the target protein.

In another embodiment, in step 4, arabinose is added at a final concentration of 0.1 M to induce the expression of the target protein.

In another embodiment, in step 4, the IPTG solution has a final concentration of 1 mM and is added to start the expression of the fusion enzyme.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention.

In the drawings.

DETAILED DESCRIPTION OF THE ILLUSTRATED EMBODIMENTS

Reference will now be made in detail to embodiments of the present invention, example of which is illustrated in the accompanying drawings. The following examples illustrate the present invention, but the present invention is not limited to the following examples.

The protein extraction method of the present invention includes:

Step 1: Combining a penetrating peptide CPP gene having a sequence as set forth in SEQ ID NO: 1 and a bacterial lyase T4L gene having a sequence as set forth in SEQ ID NO: 2 through a flexible linker peptide GGGGS gene having a sequence as set forth in SEQ ID NO: 3 to form a fusion enzyme CPP-T4L gene having a sequence as set forth in SEQ ID NO: 4.

Step 2: Inserting the fusion enzyme CPP-T4L gene to an *E. coli* expression vector pGS21a by cloning to construct an expression vector pGS21a-CPP-T4L, and transferring the expression vector pGS21a-CPP-T4L into *E. coli* BL21* (DE3) by a calcium chloride method to form a recombinant host strain.

Step 3: Inserting a target protein gene X into a pBAD/His vector to obtain a target protein expression vector, and transferring the target protein expression vector into a recombinant host strain to construct a recombinant expression strain.

Step 4: In the expression system, first adding arabinose with a final concentration of 0.1 M to induce the expression of the target protein; after the expression is completed, adding a IPTG solution at a final concentration of 1 mM to the expression system to start the expression of the fusion enzyme and release the target protein.

Step 5: After filtering to remove cell residues, collecting the cell lysis supernatant to obtain the target protein.

Example 1

Figure 1:
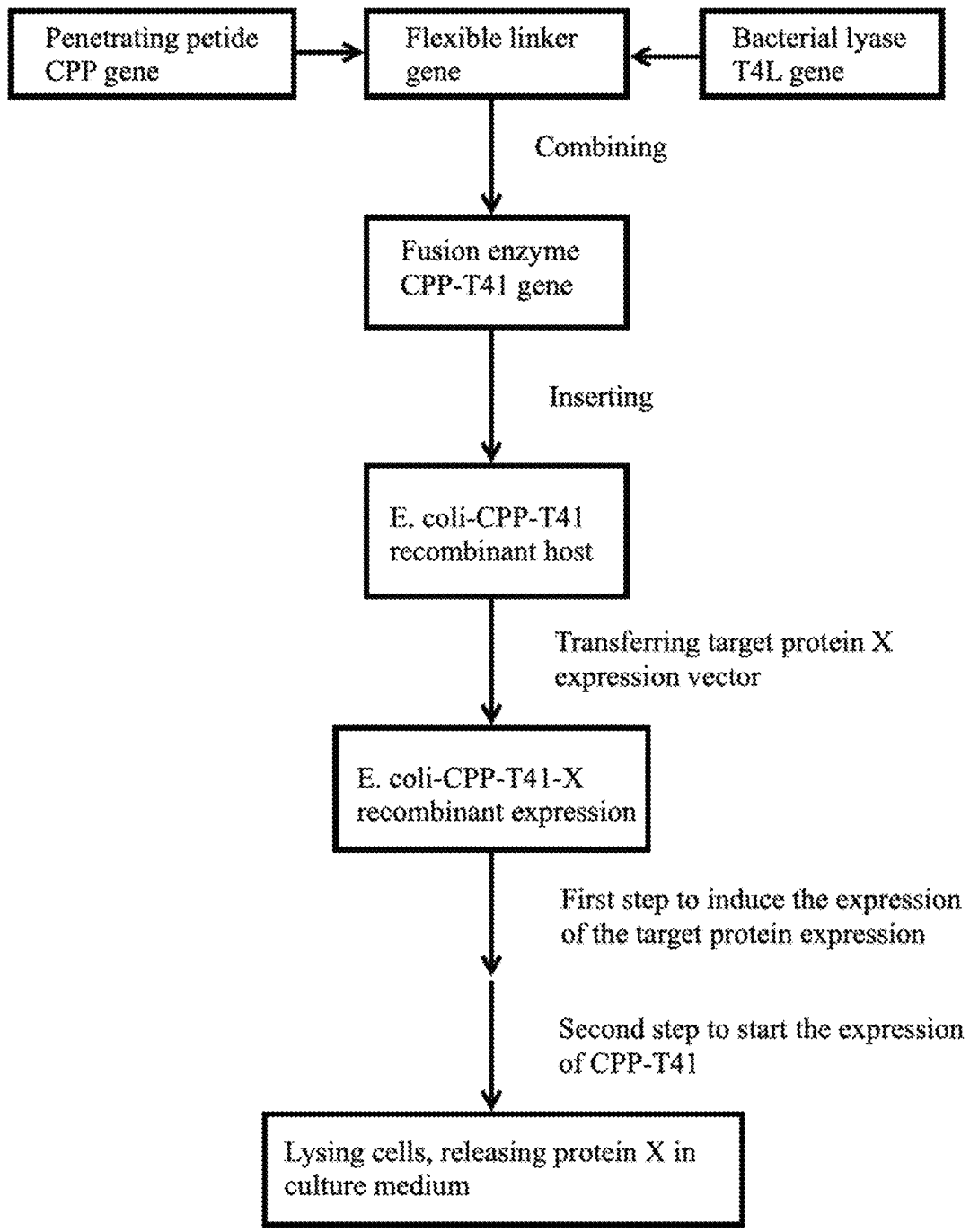
FIG. 1 is a flow chart of the protein extraction method disclosed in the present invention.

Example 1 is an example of constructing a lysing strain. Referring to FIG. 1, an *Escherichia coli* Bl21*(DE3)-CPP-T4L strain was constructed, and the strain can be lysed by itself under controlled conditions, i.e., *E. coli* BL21*(DE3)-CPP-T4L-pGS21a-pBAD-LST being lysed after expressing lysostaphin (LST) under controlled conditions.

(1) First, the penetrating peptide gene CPP and the cell lyase T4L gene were connected through the flexible linker gene GGGGS, and the fusion enzyme CPP-T4L gene was obtained by PCR technology.

(2) Second, the fusion enzyme CPP-T4L gene was inserted into an engineered strain of *Escherichia coli*. In this example, *Escherichia coli* BL21*(DE3) was used as the test strain, and the transformation method was a chemical transformation method using $CaCl_2$. After this step was completed, the target strain Bl21*(DE3)-CPP-T4L was obtained, and the activity-inducing substance IPTG (isopropyl-β-D-thiogalactopyranoside) can effectively induce the lysis of the strain.

(3) Construction of the target protein expression vector: In this example, the lysostaphin LST expression vector was constructed. In actual operation, the LST gene was inserted into the plasmid pBAD/His to obtain the LST expression vector pBAD-LST. The activity inducing substance arabinose effectively induced the expression of LST gene. In this step, a double enzyme digestion method was used to insert the LST gene to obtain the expression vectors, Ndel and Xhol, respectively.

(4) The LST expression vector pBAD-LST obtained in step (3) was transferred into Bl21*(DE3)-CPP-T4L bacteria, using the $CaCl_2$ chemical transformation method, to obtain the target strain Bl21*(DE3)-CPP-T4L-pGS21a-pBAD-LST. To ensure that the experimental results were comparable, the LST expression vector was transformed into the original BL21*(DE3) strain at the same time in actual operation, and the control strain Bl21*(DE3)-pGS21a-pBAD-LST was obtained.

Example 2

Example 2 is a verification example to test the actual lysis performance of the BL21*(DE3)-CPP-T4L strain constructed in Example 1 in nutrient medium LB, and the control strain was the original BL21*(DE3) strain.

The seed medium used in this example is LB liquid medium (1% sodium chloride, 1% peptone, 0.5% yeast extract); the fermentation medium used is LB liquid medium (1% sodium chloride, 1% Peptone, 0.5% yeast extract).

Figure 2:
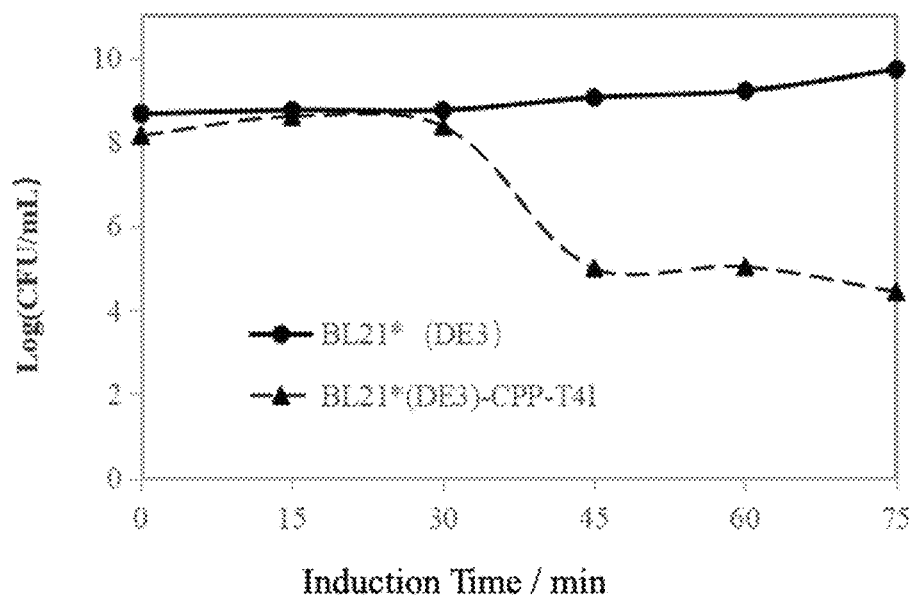
FIG. 2 is a graph showing the relationship between the number of colonies of the two strains in Example 2 and the induction time.

Experimental Steps:

(1) Inoculating BL21*(DE3) and BL21*(DE3)-CPP-T4L in LB liquid medium, and cultivating overnight at 37° C. and 200 rpm;

(2) Transferring the BL21*(DE3) and BL21*(DE3)-CPP-T4L bacteria cultured overnight in the LB liquid medium at a ratio of 1/50, and continuing cultivating at 37° C. and 200 rpm;

(3) When the bacterial solution was cultured to OD600 equal to 0.60±0.05, taking a sample and adding IPTG with a final concentration of 1 mM, and continuing cultivating at 30° C. and 200 rpm;

(4) After adding IPTG, samples were taken at 15 min, 30 min, 45 min, 60 min, 75 min;

(5) Diluting the sample to a suitable multiple and spreading it on a plate, and placing it in a 37° C. incubator for overnight culture; the next day, calculating the changes in the number of colonies of the two strains during the actual culture process. The data obtained are shown in Table 1 and FIG. 2.

TABLE 1

Changes in the number of colonies of the two strains of Example 2 with induction time

| | Log (CFU/mL) | | | | | |
|---|---|---|---|---|---|---|
| Induction Time | 0 min | 15 min | 30 min | 45 min | 60 min | 75 min |
| BL21*(DE3) | 8.67 | 8.75 | 8.76 | 9.05 | 9.22 | 9.72 |
| BL21*(DE3)-CPP-T4L | 8.15 | 8.60 | 8.37 | 5.00 | 5.03 | 4.41 |

From the above data, under the same conditions, the BL21*(DE3)-CPP-T4L strain was lysed rapidly after IPTG was added, and more than 99.99% of the cell number was lysed after 45 minutes, while the control strain continued to grow and the number of colonies continued to increase. This indicates that BL21*(DE3)-CPP-T4L has good lysis performance in LB medium.

Example 3

Example 3 is a verification example to test the actual lysis performance of the BL21*(DE3)-CPP-T4L strain constructed in Example 1 in a buffered salt solution. The control strain was the original BL21*(DE3) strain.

The seed medium used in this example was LB liquid medium (1% sodium chloride, 1% peptone, 0.5% yeast extract); the fermentation medium used was NPB (1.37 M sodium chloride, 18 mM potassium dihydrogen phosphate), 27 mM potassium chloride, 100 mM disodium hydrogen phosphate)+10% LB liquid medium (1% sodium chloride, 1% peptone, 0.5% yeast extract).

Figure 3:
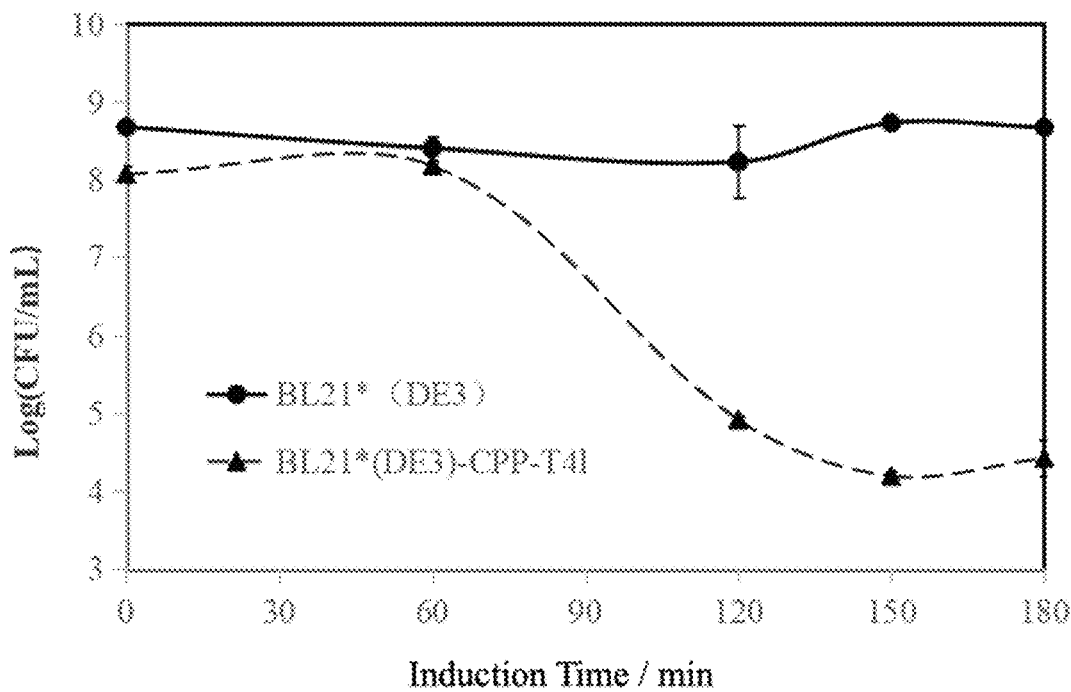
FIG. 3 is a graph showing the relationship between the number of colonies of the two strains in Example 3 with the induction time.

Experimental Procedure:

(1) Inoculating BL21*(DE3), BL21*(DE3)-CPP-T4L in LB liquid medium, and cultivating overnight at 37° C. and 200 rpm;

(2) Transferring the BL21*(DE3) and BL21*(DE3)-CPP-T4L bacteria cultured overnight in the LB liquid medium at a ratio of 1/50, and continuing cultivating at 37° C. and 200 rpm;

(3) When the bacterial solution was cultured to OD600 equal to 0.6±0.05, the cells were collected by centrifugation at 5000 rpm for 10 min, the supernatant was removed and the cell pellet was resuspended with the same volume of NPB+10% LB solution. A sample was taken and added with the activity-inducing substance IPTG with a final concentration of 1 mM, continuing cultivating at 30° C. and 200 rpm;

(4) After adding IPTG, samples were taken at 60 min, 120 min, 150 min, 180 min;

(5) Diluting the sample to a suitable multiple and spreading it on a plate, and placing it in a 37° C. incubator for overnight culture; the next day, calculating the changes in the number of colonies of the two strains during the actual culture process. The data obtained are shown in Table 2 and FIG. 3.

TABLE 2

Changes in the number of colonies of the two strains of Example 3 with induction time

| Induction Time | Log (CFU/mL) | | | | |
|---|---|---|---|---|---|
| | 0 min | 60 min | 120 min | 150 min | 180 min |
| BL21*(DE3) | 8.68 | 8.40 | 8.23 | 8.73 | 8.67 |
| BL21*(DE3)-CPP-T4L | 8.07 | 8.18 | 4.92 | 4.19 | 4.42 |

From the above data, under the same conditions, the test strain BL21*(DE3)-CPP-T4L was lysed in a large amount after IPTG was added, and over 99.99% of the cell number was lysed in 60 minutes, while the control strain continued to grow and the number of colonies increased slowly. It indicates that BL21*(DE3)-CPP-T4L has good lysis performance in NPB buffer solution.

Example 4

Example 4 is a verification example to test the actual performance of the Bl21*(DE3)-CPP-T4L-pGS21a-pBAD-LST strain constructed in Example 1 for expressing LST protein. The control strain is Bl21*(DE3)-pGS21a-pBAD-LST original strain.

The seed medium used in this example was LB liquid medium (1% sodium chloride, 1% peptone, 0.5% yeast extract); the fermentation medium used was LB liquid medium (1% sodium chloride, 1% Peptone, 0.5% yeast extract).

Test experiment steps:

(1) Inoculating Bl21*(DE3)-pGS21a-pBAD-LST and Bl21*(DE3)-CPP-T4L-pGS21a-pBAD-LST in LB liquid medium, respectively, and adding Amp antibiotics at a final concentration of 1 mM to maintain plasmid stability; cultivating overnight at 200 rpm;

(2) In LB liquid medium, transferring the overnight cultured Bl21*(DE3)-pGS21a-pBAD-LST, Bl21*(DE3)-CPP-T4L-pGS21a-pBAD-LST bacterial solution at a ratio of 1/50, and adding Amp antibiotic with a final concentration 1 mM to maintain plasmid stability, continuing cultivating at 37° C. and 200 rpm;

(3) When the bacterial solution was cultured to OD600 equal to 0.6±0.05, arabinose with a final concentration of 10 mM was added for induction, and fermented for 3 hours at 30° C. and 200 rpm;

(4) 3 After hours, IPTG with a final concentration of 1 mM was added to induce the expression of the fusion enzyme CPP-T4L, and cultured at 30° C. and 200 rpm until the cells were lysed;

(6) The control strain Bl21*(DE3)-pGS21a-pBAD-LST was fermented and the LST protein was extracted and purified by a traditional ultrasonic disruption method. The test strain Bl21*(DE3)-CPP-T4L-pGS21a-pBAD-LST was fermented directly in the fermentation solution. LST protein was purified in medium;

(7) The protein concentration was measured by a BSA (bovine serum albumin) method, and the data obtained are shown in Table 3.

TABLE 3

Concentration of protein obtained in Example 4

| Protein (Strain) | Concentration (µg/mL) |
|---|---|
| LST (B121*(DE3)-CPP-T4L-pGS21a-pBAD-LST) | 27.30 ± 0.13 |
| LST (B121*(DE3)-pGS21a-pBAD-LST) | 22.95 ± 0.25 |

According to the above data, after the same fermentation operation, the test strain Bl21*(DE3)-CPP-T4L-pGS21a-pBAD-LST did not need to perform cell lysis operation, which saves manpower, material resources and time; the concentration of harvested protein also was 84% of that of the control strains. It indicates the self-lysis system disclosed in the present invention has a good effect.

Example 5

Example 5 is a verification example, testing the difference in the activity of the LST proteins expressed in Example 4. First LST protein directly purified from the culture medium after fermentation of the Bl21*(DE3)-CPP-T4L-pGS21a-pBAD-LST strain. Bl21*(DE3)-pGS21a-pBAD-LST strain was fermented to extract and purify second LST protein by ultrasonic disruption. The LST proteins are a lysostaphin. Therefore, in this example, the number of *Staphylococcus aureus*-6538 bacteria killed by the LST proteins was used as an indicator to compare their activity differences.

The two proteins were diluted to different concentrations, and simultaneously incubated with the bacterial solution of *Staphylococcus aureus* ATCC6538 in the early stage of the index. Control: changing the proteins to an equal volume of PBS solution (137 mM NaCl, 2.7 mM KCl, 10 mM $Na_2HPO_4$, 2 mM $KH_2PO_4$). The incubation conditions were 30° C. and rotation speed was 120 rpm.

Figure 4:
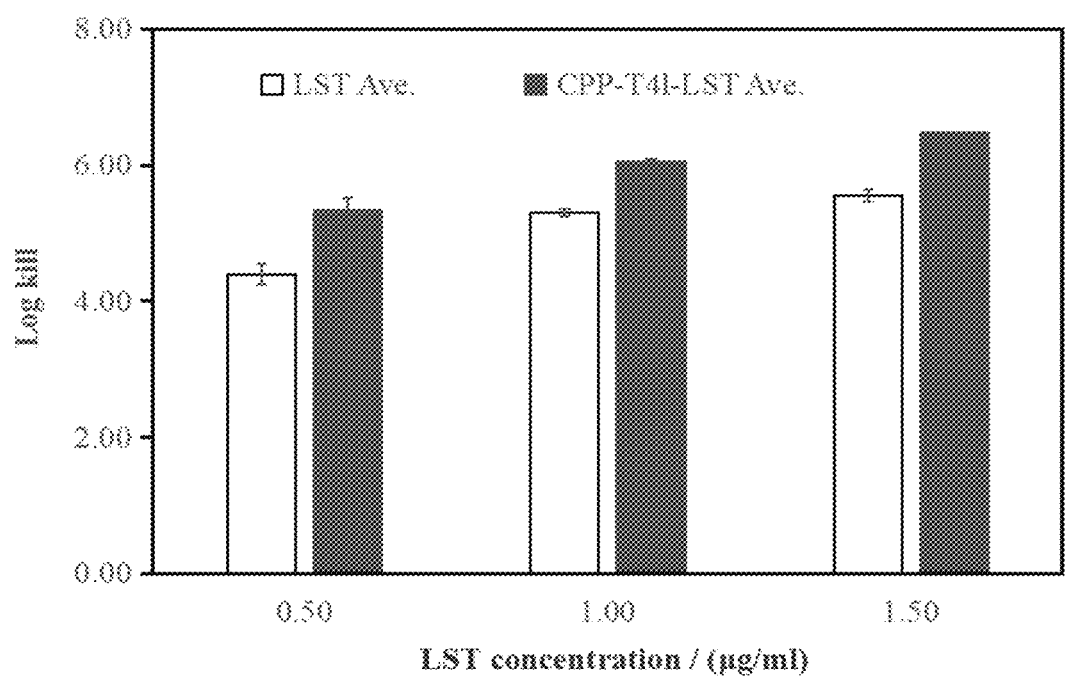
FIG. 4 is a graph showing different concentrations of proteins at which *Staphylococcus aureus* ATCC6538 was killed.

After the incubation, a dot plate experiment was used to calculate the number of *Staphylococcus aureus* ATCC6538 killed at different concentrations of protein, and the data obtained are shown in Table 4 and FIG. 4.

TABLE 4

The number of *Staphylococcus aureus* ATCC6538 of different killed at concentrations of proteins

| | Absolute number of ATCC6538 killed | | | |
|---|---|---|---|---|
| Protein | LST (B121*-pGS21a-pBAD-LST) | | LST (B121*-CPP-T4L-pGS21a-pBAD-LST) | |
| Concentration (µg/mL) | Average | Standard Deviation | Average | Standard Deviation |
| 0.5 | 4.40 | 0.15 | 5.33 | 0.19 |
| 1.00 | 5.3 | 0.06 | 6.06 | 0.04 |
| 1.50 | 5.56 | 0.09 | 6.48 | 0.01 |

From the above data, under the same conditions, the LST protein expressed by Bl21*(DE3)-CPP-T4L-pGS21a-pBAD-LST is more effective than the LST expressed by Bl21*(DE3)-pGS21a-pBAD-LST. The number of *Staphylococcus aureus* killed by LST protein expressed by Bl21*(DE3)-CPP-T4L-pGS21a-pBAD-LST is more than that of Bl21*(DE3)-pGS21a-pBAD-LST, which indicates that the protein extraction method disclosed in the present invention is effective.

The protection scope of the present invention is not limited to the above-mentioned embodiments. For those of ordinary skill in the art, if various changes and modifications made to the present invention fall within the scope of the claims of the present invention and equivalent technical scope, the intention of the present invention includes these changes and deformations.

Finally, it should be noted that the above embodiments are only used to illustrate the technical solutions of the present invention and not to limit it. Although the present invention has been described in detail with reference to the above embodiments, those of ordinary skill in the art should understand that: modifications or equivalent replacements of specific embodiments without departing from the spirit and scope of the present invention shall be covered by the scope of the claims.

The invention does not require a protein extraction method for lysing cells. The method genetically transforms *Escherichia coli*, and constructs an engineered strain that can be lysed by itself under controlled conditions. After the strain normally expresses the target protein, the autolyzed gene with the function of lysing *Escherichia coli* is induced to express, so that the bacterial cell is rapidly lysed, and the target protein in the cell is effectively released, so as to achieve the purpose of extracting the protein without lysing the cell. The strain constructed by the present invention was subjected to lysis and lysostaphin LST expression performance test, and the results showed that the concentration of the bacterial cell was reduced by more than 99% after the lysis was induced, and the extracellular protein content could reach 84% of the control group.

What is claimed is:

1. A method for extracting a target recombinant protein from a recombinant host strain, comprising:
   step 1: combining a penetrating peptide CPP gene (SEQ ID NO:1), and a bacterial lyase T4L gene (SEQ ID NO:2) by a flexible linker peptide gene (SEQ ID NO: 3) to form a fusion enzyme encoded by CPP-T4L gene (SEQ ID NO:4);
   step 2: inserting the CPP-T4L gene into an expression vector, and then transferring the expression vector into an expression strain to obtain a recombinant host strain;
   step 3: inserting a target protein expressing gene into a target protein expression vector, and then into said recombinant host strain;
   step 4: in an expression system comprising said recombinant host strain,
   first, inducing the target protein expressing gene and allowing for complete target gene expression;
   second, adding an IPTG (isopropyl P-D-1-thiogalactopyranoside) solution as a lysis inducer, to the expression system to start releasing the expressed target protein in said recombinant host strain into solution; and
   step 5: filtering the expression system solution and collecting the supernatant containing the recombinant target protein.

2. The method according to claim 1, wherein in step 2, the vector comprising the CPP-T4L gene is *Escherichia coli* expression vector pGS21a, and the recombinant host strain is *Escherichia coli* BL21*(DE3).

3. The method according to claim 1, wherein in step 2, the vector comprising the CPP-TL4 gene is transferred into the recombinant host strain by calcium chloride method.

4. The method according to claim 1, wherein in step 3, the target protein expression vector is a pBAD/His vector.

5. The method according to claim 1, wherein the target protein is lysostaphin, and arabinose is added in step 4 to induce the expression of the target protein.

6. The method according to claim 5, wherein in step 4, arabinose is added at a final concentration of 0.1 mM to induce the expression of target protein.

7. The method according to claim 1, wherein in step 4, the IPTG solution has a final concentration of 1 mM and is added to start the expression of the fusion enzyme.

* * * * *